(12) United States Patent
Lizzi et al.

(10) Patent No.: US 10,654,666 B2
(45) Date of Patent: May 19, 2020

(54) SYSTEM WITH IMPROVED PLATE DESTACKING

(71) Applicant: BD KIESTRA B.V., Drachten (NL)

(72) Inventors: Michael Justin Lizzi, Stewartstown, PA (US); Lukas Blaauw, Leeuwarden (NL); Timothy Roy Hansen, Spring Grove, PA (US); Freerk H. Van Der Werff, De Westereen (NL); Jurjen Sinnema, Joure (NL); Jordan Brown, Ontario (CA); James Glen Burmaster, Ontario (CA); Rui Goncalves, Ontario (CA); Milenko Lukic, Ontario (CA); Nino Orucevic, Ontario (CA); Martin John Juritsch, Ontario (CA)

(73) Assignee: BD KIESTRA B. V., Drachten (NL)

( * ) Notice: Subject to any disclaimer, the term of this patent is extended or adjusted under 35 U.S.C. 154(b) by 0 days.

(21) Appl. No.: 15/572,719

(22) PCT Filed: May 13, 2016

(86) PCT No.: PCT/US2016/032352
§ 371 (c)(1),
(2) Date: Nov. 8, 2017

(87) PCT Pub. No.: WO2016/183441
PCT Pub. Date: Nov. 17, 2016

(65) Prior Publication Data
US 2018/0099823 A1   Apr. 12, 2018

Related U.S. Application Data

(60) Provisional application No. 62/160,982, filed on May 13, 2015.

(51) Int. Cl.
*B65G 59/06* (2006.01)
*B65G 59/10* (2006.01)
(Continued)

(52) U.S. Cl.
CPC ......... *B65G 59/106* (2013.01); *B65G 59/063* (2013.01); *C12M 23/10* (2013.01);
(Continued)

(58) Field of Classification Search
CPC .... B65G 59/105; B65G 59/10; B65G 59/106; B65G 59/063; B65G 47/252;
(Continued)

(56) References Cited

U.S. PATENT DOCUMENTS 630,187 A * 8/1899 Cunningham ....... B65G 59/063
 414/797.5
636,245 A * 11/1899 Cunningham ....... B65G 59/063
 414/797.5
(Continued)

FOREIGN PATENT DOCUMENTS

EP   1267203 A2   12/2002
JP   S58113035 A   7/1983
WO   0066467 A1   11/2000

OTHER PUBLICATIONS

International Search Report from PCT Application No. PCT/US2016/032352 dated Jul. 22, 2016.

*Primary Examiner* — Gregory W Adams
(74) *Attorney, Agent, or Firm* — Botos Churchill IP Law LLP

(57) ABSTRACT

A separating system (1) comprises a housing (60) sized to receive a stack of articles having at least one first article (12) stacked on top of a second article (10). The system (1) also includes a lifter (20) movable into a contact position adjacent a surface (13) on the at least one first article (12). The lifter (20) is adapted to apply a lifting force to the surface (13) to lift at least a portion of the first article (12) above the contact position. An extractor (40) moves the second article (10) away from the stack of articles after the at least one first article (12) has been lifted above the contact position by the
(Continued)

lifter (20). The housing (60) prevents the at least one first article (12) from moving with the second article (10) when the second article (10) is moved by the extractor (40) and guides the stack of articles downward after the second article (10) is moved away.

18 Claims, 14 Drawing Sheets

(51) Int. Cl.
  *C12M 1/22* (2006.01)
  *C12M 3/00* (2006.01)
  *C12M 1/00* (2006.01)
  *G01N 35/04* (2006.01)

(52) U.S. Cl.
  CPC ............ *C12M 23/48* (2013.01); *C12M 99/00* (2013.01); *G01N 2035/0425* (2013.01)

(58) Field of Classification Search
  CPC ....... B65G 59/067; B65B 43/44; B65B 43/48; C12M 23/10; C12M 23/48; C12M 99/00; G01N 2035/0425; G07F 11/14; G07F 11/16; G07F 11/24
  USPC ..... 221/251, 268, 293, 298; 414/795.6, 796, 414/797.4, 797.5, 797.9, 798.1
  See application file for complete search history.

(56) References Cited

U.S. PATENT DOCUMENTS

| | | | | |
|---|---|---|---|---|
| 1,330,964 A | * | 2/1920 | Wheelwright | B65B 35/02 221/297 |
| 1,866,369 A | * | 7/1932 | Podel | B67B 3/22 221/238 |
| 2,453,545 A | * | 11/1948 | Simpson | B21D 43/24 414/797.5 |
| 2,553,683 A | * | 5/1951 | Smith | B65G 59/062 198/418.3 |
| 2,770,392 A | * | 11/1956 | Roberts | B65B 35/40 221/1 |
| 3,289,861 A | * | 12/1966 | Carle | B65G 59/106 221/225 |
| 3,702,103 A | * | 11/1972 | Price | B21D 43/24 221/268 |
| 3,752,361 A | * | 8/1973 | VanLinder | B65G 59/062 221/210 |
| 3,869,048 A | * | 3/1975 | Takahashi | B65G 59/063 221/173 |
| 3,908,341 A | * | 9/1975 | Conti | B67B 3/06 53/314 |
| 3,920,152 A | * | 11/1975 | Shields | B65B 37/08 221/236 |
| 4,013,179 A | * | 3/1977 | Fluck | B65B 23/14 221/251 |
| 4,043,460 A | * | 8/1977 | Steele | B65G 57/303 414/795.2 |
| 4,431,404 A | * | 2/1984 | Cobb | F27D 13/00 34/144 |
| 4,457,665 A | * | 7/1984 | Fluck | B65G 59/067 221/262 |
| 4,709,912 A | * | 12/1987 | Illig | B65H 3/02 221/259 |
| 4,718,808 A | * | 1/1988 | Hoshino | B65G 59/067 221/274 |
| 4,809,881 A | * | 3/1989 | Becker | B65G 59/103 141/172 |
| 4,865,515 A | * | 9/1989 | Dorner | B65G 57/302 414/788.2 |
| 5,105,980 A | | 4/1992 | Hofmann | |
| 5,788,114 A | * | 8/1998 | Perego | B65B 25/002 221/11 |
| 5,842,598 A | * | 12/1998 | Tsuchida | B65G 59/105 221/258 |
| 6,193,102 B1 | * | 2/2001 | Bevirt | G01N 35/028 221/197 |
| 2010/0035338 A1 | | 2/2010 | Bruno et al. | |
| 2015/0023773 A1 | * | 1/2015 | Redman | B65G 59/063 414/797.5 |

* cited by examiner

SYSTEM WITH IMPROVED PLATE DESTACKING

CROSS-REFERENCE TO RELATED APPLICATION

The present application is a national phase entry under 35 U.S.C. § 371 of International Application No. PCT/US2016/032352 filed May 13, 2016 published in English, which claims priority from U.S. Provisional Application No. 62/160,892 filed May 13, 2015, all of which are incorporated herein by reference.

BACKGROUND OF THE INVENTION

The present invention relates to a plate separator or destacking system used to remove an article (e.g., a culture plate or dish) from a stack of such articles; or, more particularly, to separate a first article (or culture plate or dish) in the stack of said articles from at least one second article stacked on top of the first article.

Biological samples such as body fluids (e.g., blood, urine, etc.) water samples, food samples, soil samples, etc. are frequently tested for the presence or absence of microorganisms (e.g., bacteria, fungi, etc.). Such tests typically require the samples to be combined with nutrient media to cultivate the growth of a sufficient amount of microorganisms in the sample to allow for reliable detection. Testing samples for evidence of microbial growth has historically been a manual process. Lab technicians will prepare culture plates, inoculate them with sample, place the inoculated plates in an incubator and periodically check the plates for the growth of colonies of bacteria. When there is evidence of microbial growth, a portion of the colony is picked. The picked sample is then combined with solution for downstream testing to determine the type of microorganism and what susceptibilities and resistances the microorganisms might have regarding antibiotics.

Because the manual laboratory testing is labor-intensive, efforts are underway to automate some or all of these laboratory processes. Automated processing is configured to prepare and monitor many plates in assembly line fashion. Platforms for automated culture plate processing provide an inventory of non-inoculated plates with growth media that are selected for processing. The platform, in response to an entered order takes a culture plate from inventory, inoculates the plate with the sample corresponding to the order, incubates the plate and periodically inspects the plate for evidence of microbial growth. All of these steps can be accomplished using automated handling of the plates, the sample and the reagents used to prepare and process the plate. These automated sample processing platforms are referred to as total lab automation.

Such automated medical testing systems typically stack the inventory of culture plates (containers such as petri dishes) for efficiency of storage and ease of access and automated processing. Although stored in stacks, each plate is processed individually. Consequently, the automated system must be able to remove individual plates from the stack so as to convey each plate to a designated testing location remote from the stack. In such systems, since each plate must be identified and tracked, the plates are often processed in the order they are provided to the system ("first in first out" or FIFO). In terms of automated processing of stacked articles, this means that the articles are added to the top of the stack and removed from the bottom, or vice-versa.

Removing a plate from the stack can destabilize the stack, damage the plate, cause the lid to separate from the plate, etc. Removing more than one plate at time can cause the plates to be processed out of order. This could result in the plate being inoculated with a sample intended for a different plate, wasting sample, processing time and the plate itself. Such errors can therefore compromise the integrity of the plate processing, cause cross-contamination, etc. Similarly, such problems can arise in other contexts where stacked articles are removed from the stack one by one for further processing.

Automated apparatus used to store and retrieve plates are known. Such devices receive and store plates in a stack, with automated mechanisms to add plates to and remove plates from the stack. One such device is the SorterA module that is part of the InoqulA automated apparatus for sample preparation that is sold commercially by Becton Dickinson.

Accordingly, apparatus for removing an article from a stack of articles without disturbing the stability of the remaining articles in the stack are sought.

SUMMARY OF THE INVENTION

Aspects of the present invention facilitate removing an article from a stack of articles using automation. Typically, the removed article is the first or bottom-most article in the stack, although the invention is not limited to removing the bottom-most article from the stack. These aspects allow for removing the article without disturbing the stability of the one or more articles that remain in the stack after the first article has been removed. For example, the stack of articles may be retained in a housing that holds the stack steady as the first article is removed.

Typically, the top and bottom surfaces of each article have a nesting feature adapted to promote "nested stacking" of the articles in the stack. In one example of this nesting feature, a nesting feature on the bottom of a top article may be adapted to mate with a nesting feature on the top of a bottom article. Nested stacking delivers many benefits. For example, it allows the entire stack of articles to be moved along a surface as a single unit that is more stable so that the articles remain stacked even if subjected to vibration and other disruptive forces typical of automated processing.

Removing nested articles from the stack of articles is problematic in that the plate to be removed must be separated from the other plates either above or below to be removed from the stack without carrying along with it the plate above it or below it, which can destabilize the stack or remove more than one plate from the stack. Therefore, other aspects of the present invention vertically separate the article being removed from other articles stacked above it. The separated article is then pushed or pulled out from under the stack. For example, the article may be separated so that an extraction device may be used to push the first article from underneath the stack of articles for transport to a remote testing location.

Other aspects of the present invention are directed to various means for executing the movements described herein. For example, an exemplary lifting mechanism is described as a means for lifting at least one second or upper article and pushing the first article away from the one or more lifted second articles. Preferably, this lifting mechanism is adapted to execute these movements in a continuous, fluid motion to avoid disrupting the contents of any particular first or second article contained within the stack of articles.

DETAILED DESCRIPTION

Figure 1:
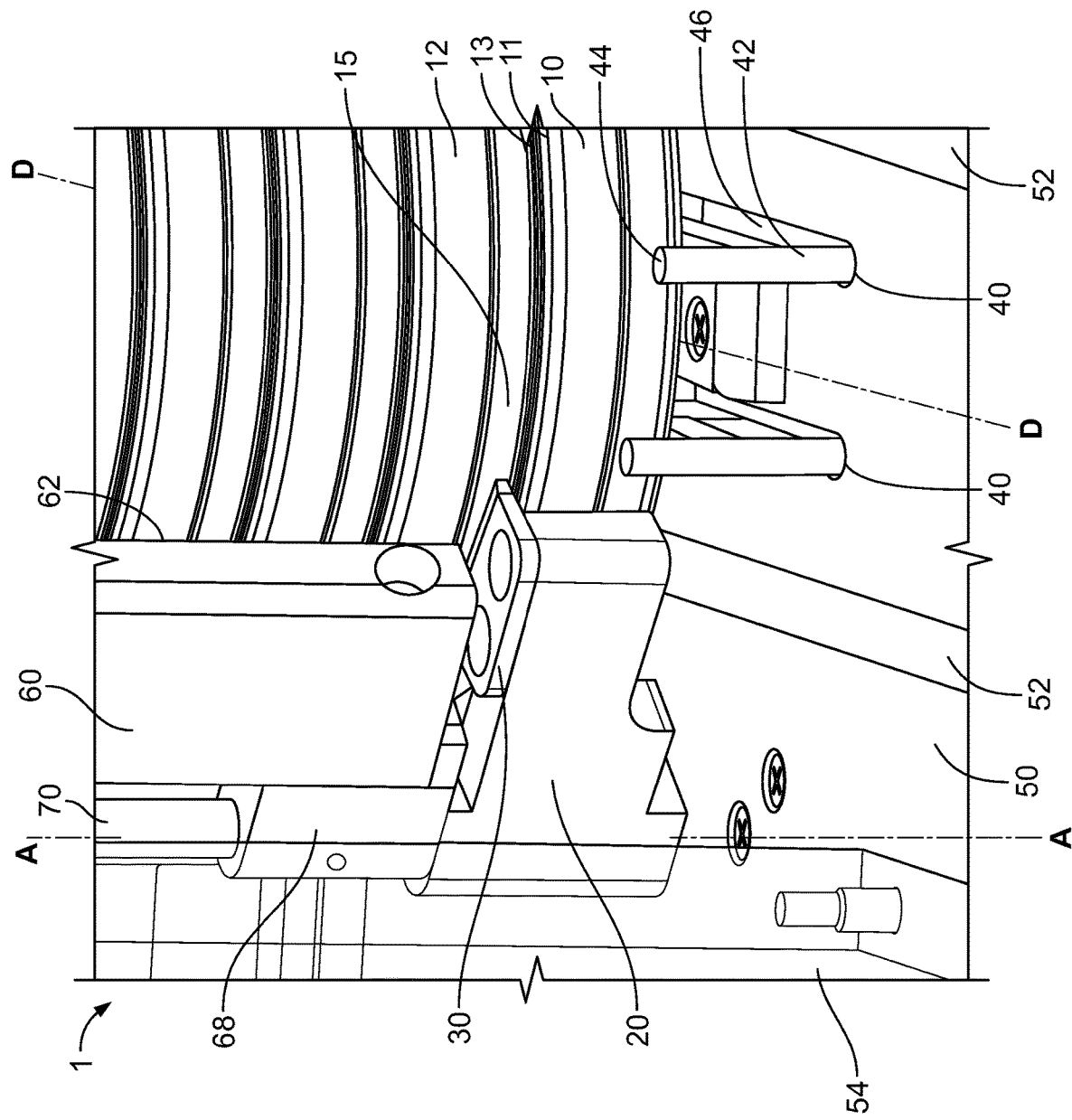
FIG. 1 is a perspective view of the article destacking system of the present invention.

The present invention is directed to various embodiments of an article removal system 1 for removing at least one article from a stack of articles. Referring to FIGS. 1 and 14, the stack of articles is comprised of at least one upper or second article 12 stacked on top of at least one lower or first article 10. In one embodiment, the first and second articles 10 and 12 are culture plates (e.g. petri dishes). In other embodiments, the system 1 is integrated with a total lab automated platform for processing the articles from inoculation through evaluation. Desirably, system 1 facilitates the downstream processing of cultures grown in the culture plates 10 and 12 by allowing each plate to be efficiently removed from the stack.

Figure 14A:
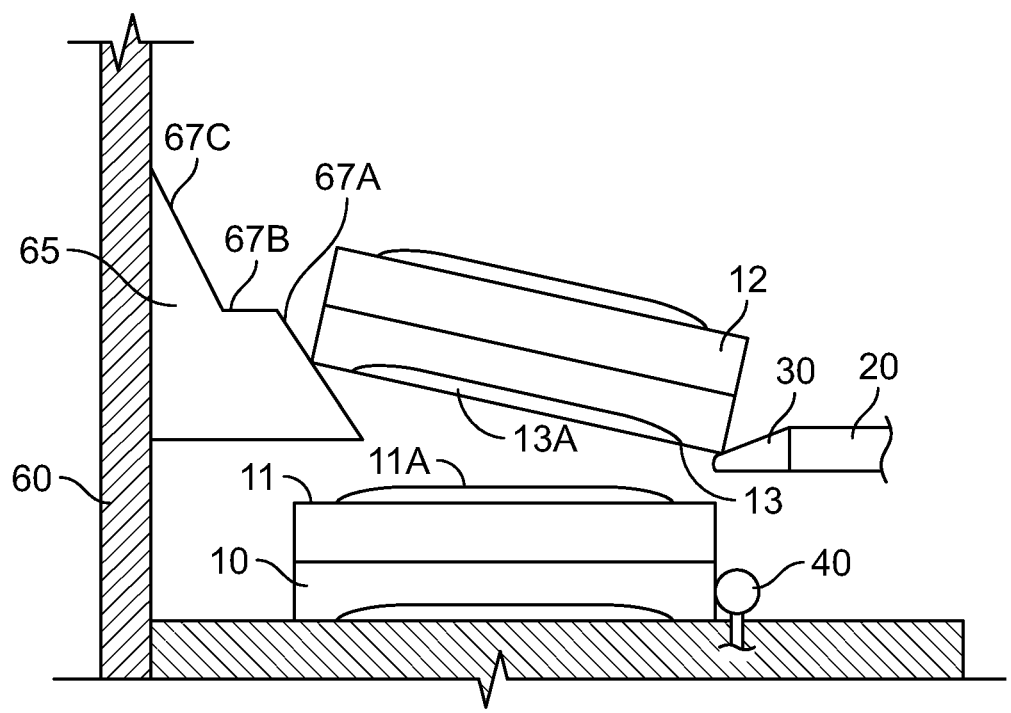
FIG. 14A depicts a profile view of a portion of the embodiment of FIG. 13A with additional details regarding an element of the housing.
Figure 14B:
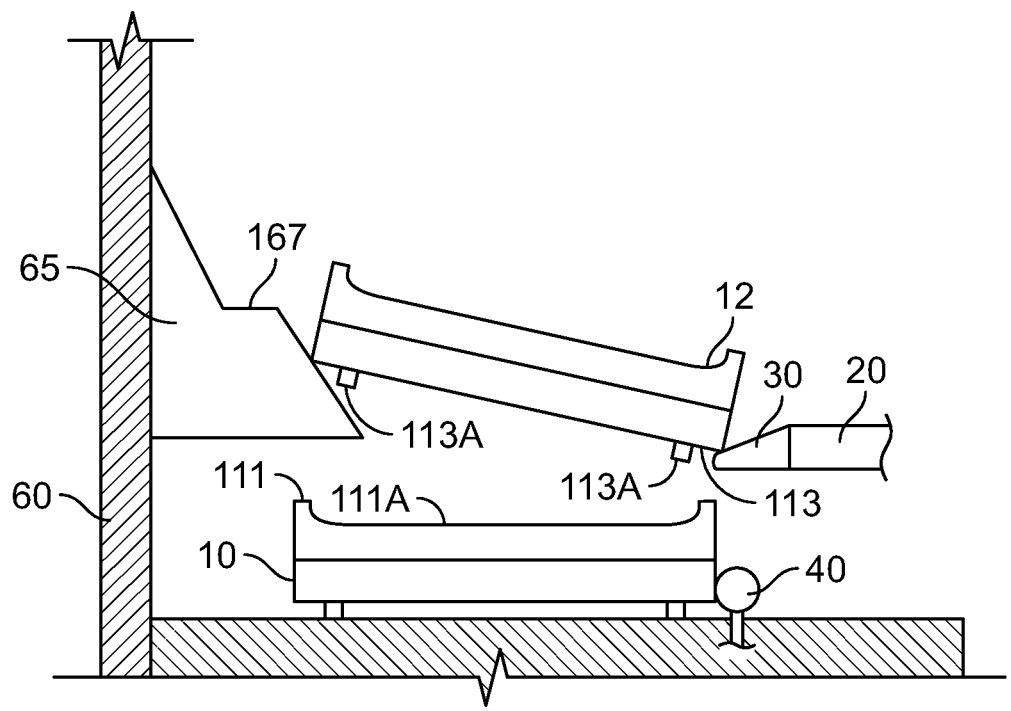
FIG. 14B depicts a profile view of an alternate embodiment of FIG. 14A.

System 1 may be used with a nested stack of articles. For example, each article 10 and 12 is illustrated in FIGS. 14A-B as being nested together with an adjacent article to provide stack stability. Various nesting features are contemplated. In FIG. 14A, first article 10 has a top surface 11 with a slightly convex portion 11A that conforms to a slightly concave portion 13A of the bottom surface 13 of second article 12. In FIG. 14B, first article 10 has a top surface 111 with a slightly concave portion 111A that is adapted to receive a ring portion 113A (shown in cross-section) of a bottom surface 113 of second article 11.

Figure 2:
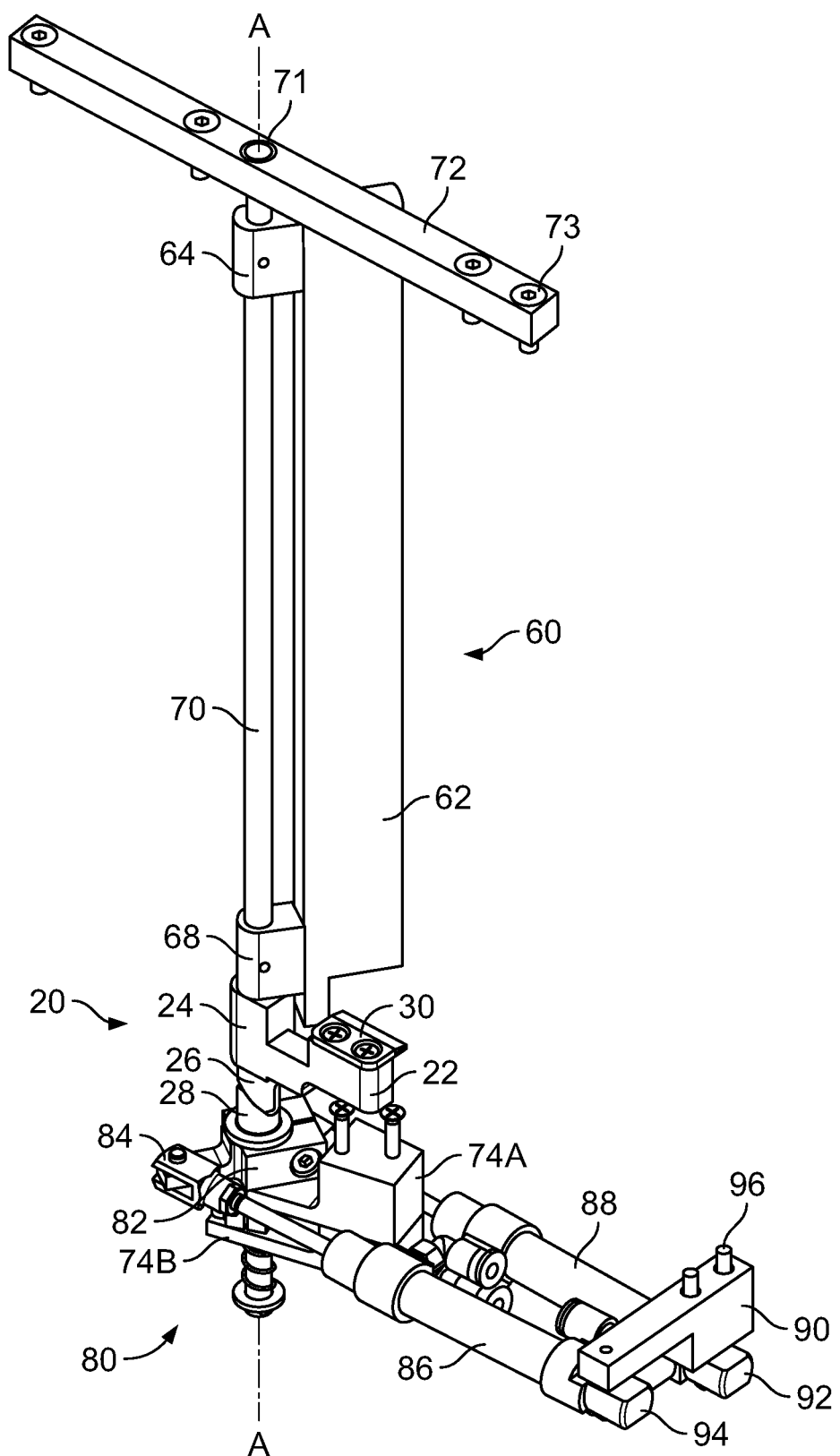
FIG. 2 is a detailed view of the lifter, moveable door, and lifting mechanism elements of the present invention.

Elements of one embodiment of system 1 are depicted in FIGS. 1-2. As shown, system 1 has a lifter 20, an extractor 40, and a housing 60. Each element 20, 40 and 60 is adapted to cooperate in moving first article 10 away from second article 12 while maintaining stack stability. As illustrated, the second article 12 is raised by the lifter 20 in a first direction parallel to the exemplary longitudinal axis A-A and then allowed to move in a second, opposite direction along axis A-A to replace first article 10. Preferably, first article 10 is replaced by second article 12 as first article 10 is moved away from the stack of articles. For example, in the embodiment of FIG. 1, first article 10 is moved away from the stack of articles in first or second direction of movement along an exemplary motion axis D-D after second article 12 is raised.

Lifter 20 is adapted to engage second article 12 and raise it at least partially above first article 10. For example, in FIG. 2, lifter 20 is movable into a contact position adjacent a contact surface 15 of second article 12. Once positioned, lifter 20 may be moved upward along exemplary axis A-A (FIG. 2) by application of a lifting force thereto. At least a portion of lifter 20 is adapted to transfer the lifting force to contact surface 15 of second article 12 (FIG. 1). The lifting force is sufficient to lift at least a portion of the second article 12 above its contact position with first article 10. Desirably, this allows first article 10 to be moved away from the stack of articles when second article 12 is in the lifted position.

Figure 5:
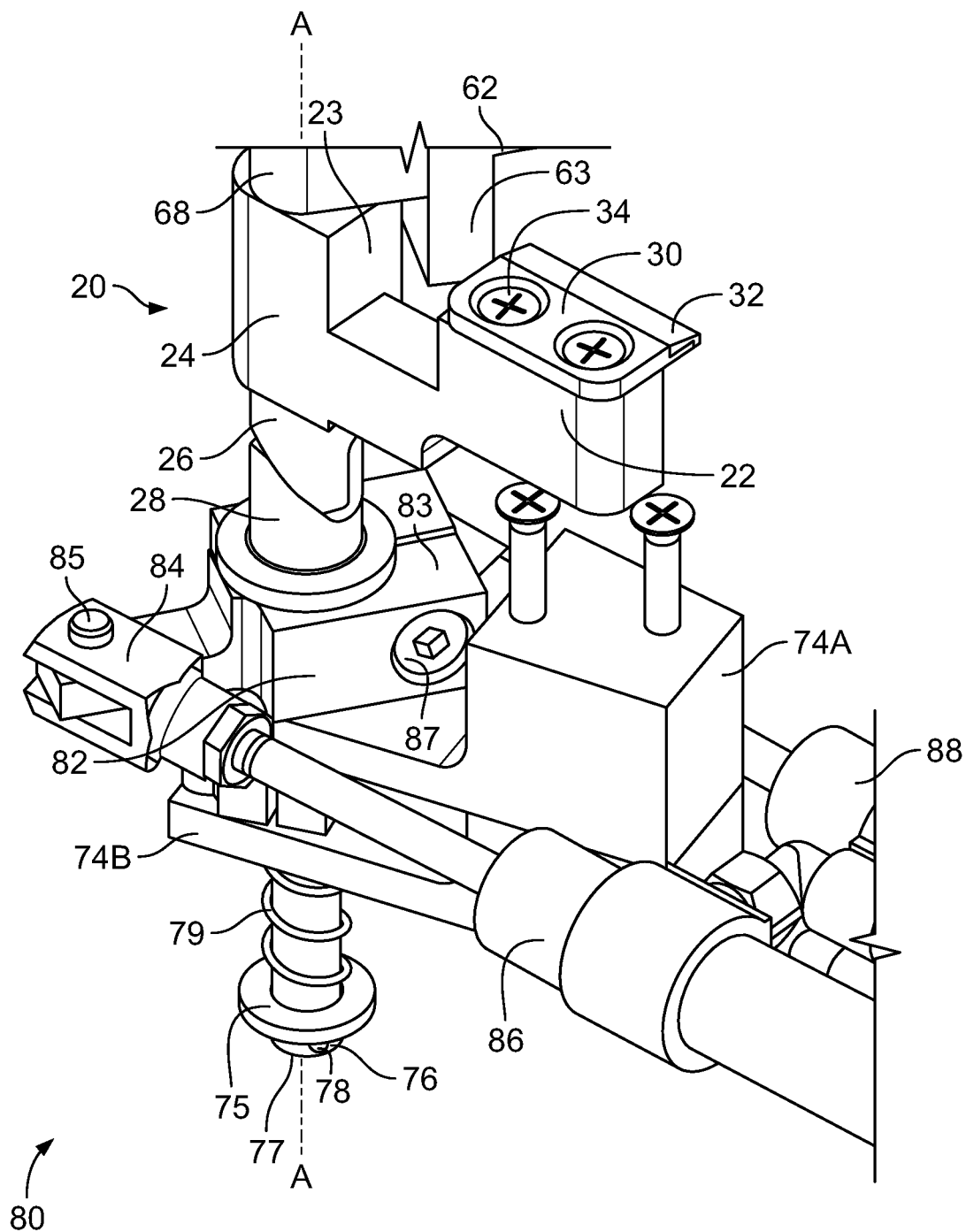
FIG. 5 is a close-up perspective view of the lifter and lifting mechanism.

In FIGS. 2 and 5, lifter 20 comprises a lifter arm 22 that is rotatable about axis A-A into the contact position. In this embodiment, lifter arm 22 spans between a lift surface 30 and an end portion 24 located opposite of lift surface 30. Lift surface 30 is adapted to engage contact surface 15 of second article 12 when lifter arm 22 is moved into the contact position. Preferably, lift surface 30 is adapted to transfer a lifting force to the contact surface 15 that is sufficient to lift or move at least a portion of second article 12, and any other second articles stacked thereon, above the contact position. Although depicted as a removable element in FIGS. 2 and 5, lift surface 30 may be integral with arm 22.

Some embodiments of lift surface 30 are optimized to transfer the lifting force described above. For example, lift surface 30 may be frictionally or mechanically engageable with second article 12. In those embodiments where the lifting force has a frictional component, the magnitude of lifting force applied by lift surface 30 is proportionate to the coefficient of friction between lift surface 30 and the contact surface 15 of article 12. To maximize the lifting force in those embodiments, lift surface 30 may have a roughened surface. Alternatively, at least a portion of lift surface 30 may be comprised of a composition selected from a group consisting of silicon, urethane, a like material, and a combination thereof. In those embodiments where the lifting force has a mechanical component, lift surface 30 may be adapted to wedge between articles 10 and 12 so as to raise article 12 by applying the lifting force to a portion of bottom surface 13. These embodiments are described below with reference to FIGS. 9A-C.

Extractor 40 moves first article 10 away from beneath the stack of articles after second article 12 has been at least partially lifted above first article 10 by lifter 20. This allows the first article 10 to be removed from the stack by destacking system 1 and then conveyed to a remote location.

In the illustrated embodiment, extractor 40 is moved along arrow D-D from a retracted position beneath first article 10 to an extraction position adjacent first article 10. Extractor 40 of FIG. 1 moves into the extraction position along arrow D-D in a first or second direction. Preferably, extractor 40 moves under the stack of articles while in the retracted position; transforms into the extraction position; and then moves oppositely in the second direction to push the first article 10 away from the stack of articles. The embodiment of extractor 40 illustrated in FIG. 1 has two retractable arms 42 that are retracted into the extraction position as they move under lower article 10. Each retractable arm 42 is contained within extractor frame 46 in the retracted position and biased to open away from frame 46 into the extraction position. This allows an end portion 44 of retractable arm 42 to push lower article 10 as extractor 40 moves in the second direction to carry article 10 away from the stack of articles.

Arms 42 are depicted in the extraction position in FIG. 1. In the illustrated embodiment, retractable arms 42 are moved into and out of the retracted position without the use of an actuator. For example, retractable arms 42 of FIG. 1 have a hinge with a spring element (not shown) that urges each arm 42 into the extraction position. Preferably, the spring element has a spring constant that is strong enough to bias arm 42 into the extraction position, yet weak enough to permit arms 42 to be forced into extractor frame 46 as extractor 40 moves past first article 10. This allows arms 42 to automatically spring into the extraction position after they have passed under first article 10. Arms 42 are configured so that when extractor 40 draws arms 42 under article 10 to move into the extraction position, each arm 42 is smoothly and easily forced into frame 46.

Figure 12A:
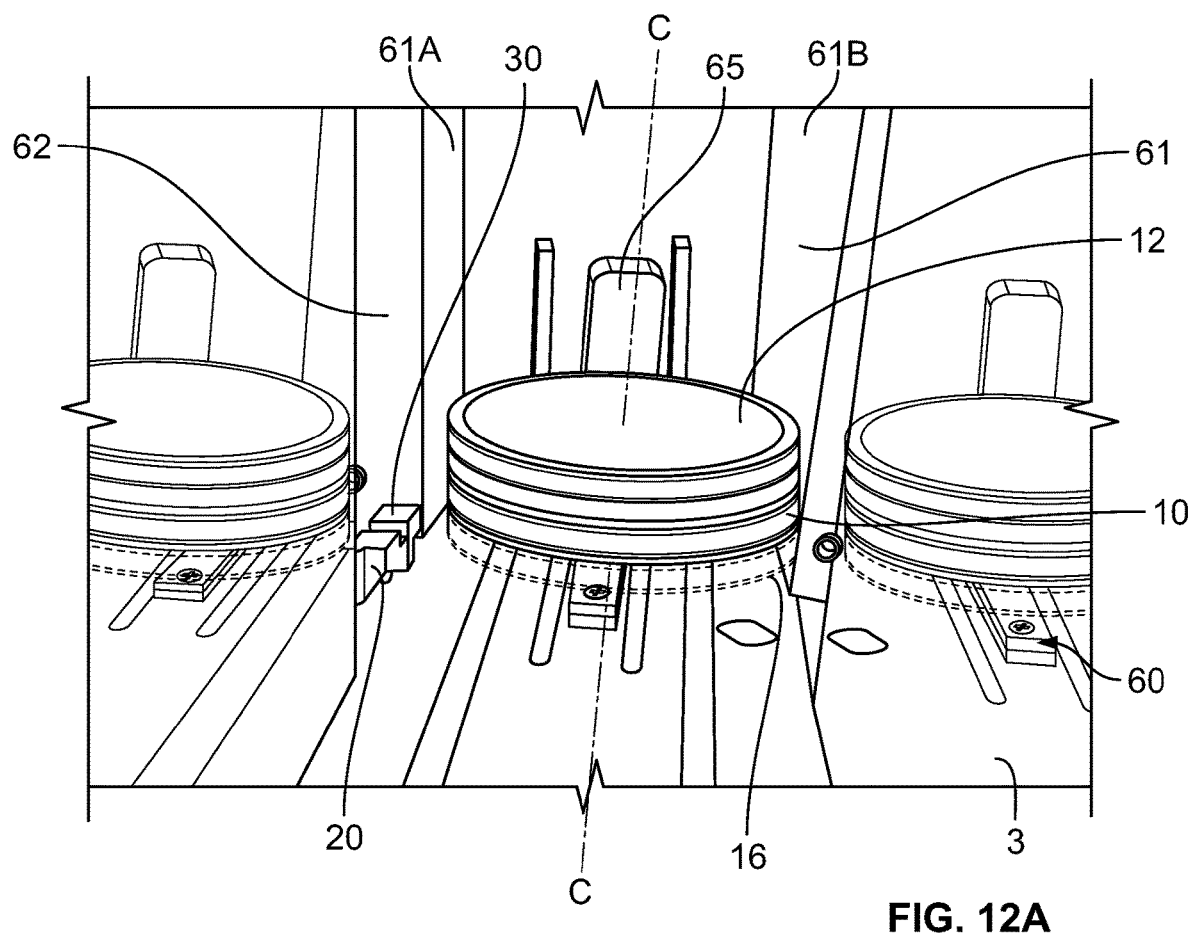
FIG. 12A provides a perspective view of the housing after the articles have been loaded therein.

Housing 60 of system 1 stabilizes the remaining articles in the stack when article 10 is moved from under the stack of articles by extractor 40. As such, housing 60 may have any number of fixed or moveable surfaces disposed oppositely around a stack perimeter 16 having an exemplary stack axis C-C (FIG. 12A). It should be appreciated that the surfaces of housing 60 described herein are exemplary. Therefore, a person of ordinary skill in the art can select many different configurations for stabilizing the stack of articles in accordance with the present invention to permit removal of first article 10 without destabilizing the stack of articles.

Figure 3:
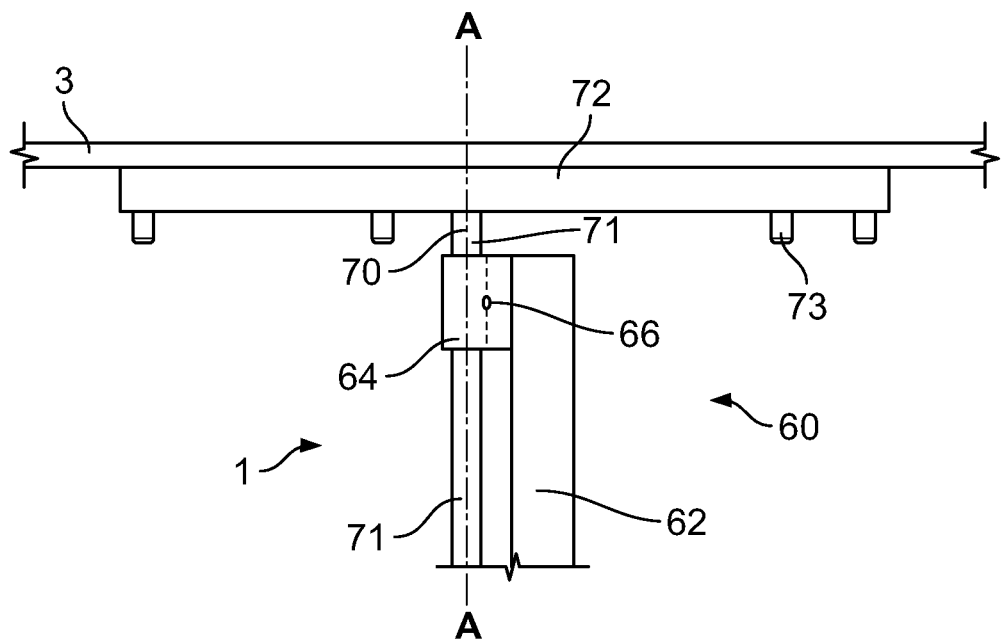
FIG. 3 is a close up view of a portion of the moveable door.

As illustrated, housing 60 has an interior surface 61 that surrounds a portion of stack perimeter 16. In FIG. 12A, housing 60 is a rigid element that is affixed to an exemplary table surface 2 (FIG. 3). Interior surface 61 is configured to stabilize the stack of articles and retain second article 12 as first article 10 is removed from the stack of articles. In this regard, interior surface 61 does not surround the entirety of the stack articles. Instead, interior surface 61 has at least two surfaces 61A and 61B that are spaced apart on opposite sides of stack perimeter 16 to allow first article 10 to pass therebetween. In some embodiments, interior surface 61 may form an opening that allows first article to pass therethrough. This allows guiding surfaces 61A and 61B, together with other elements of system 1, to cooperatively stabilize the stack.

Housing 60 also provides a means for loading the stack of articles into perimeter 16. In one embodiment, for example, the spatial arrangement of surfaces 61A and 61B permits the stack of articles to be top loaded into perimeter 16 along stack axis C-C. Preferably, surfaces 61A and 61B guide the stack of articles into perimeter 16 so as to prevent the articles from wedging between surfaces 61A and 61B, tipping over, or opening up. In complement, housing 60 also ensures that the respective nesting features of each article 10 or 12 are coaxially aligned during the loading process so as to nest together, if desired, as the stack is formed. Alternatively, as in FIG. 1, the stack of articles may be side loaded into the stack perimeter 16 along arrow D-D by a conveyor. This allows for a plurality of different stacks to be processed. For example, each of a plurality of different stacks may be arranged on the conveyor and then moved into perimeter 16 after each article in the preceding stack of articles has been moved away.

System 1 includes a moveable door 62 that cooperates with housing 60 to stabilize the stack of articles, facilitate side loading, and permit access to the stack of articles after it has been moved into stack perimeter 16. In FIG. 2, for example, door 62 is an elongated element that may be rotated about axis A-A from a stored position adjacent housing 60 into a support position adjacent the stack of articles. Rotating moveable door 62 into the support position confines the stack of articles within perimeter 16. This allows door 62, in cooperation with the interior surface 61 of housing 60, to stabilize the stack of articles as it is raised by lifter 20. The stack may be side loaded when door 62 is in the stored position. Preferably, the stack is side loaded by moving it along arrow D-D between interior surface 61 and past door 62. It may be necessary to manually adjust an article if the stack is improperly formed or disrupted after formation. These issues can be resolved by rotating moveable door 61 into the stored position so that a technician can access the stack of articles and remove the misplaced articles.

Housing 60 and moveable door 62 are made of a material, such as acrylic, that has a low coefficient of friction with articles 10 and 12. This allows the entire stack of articles to slide against the respective interior surfaces of moveable door 62 and housing 60 as second article 12 is raised. Interior surface 61 preferably has a guide element 65 that directs second article 12 as it slides upward. Guide element 65 preferably has a guide surface 67. In FIG. 14A, guide surface 67 is angled to have at least a first slope 67A, a plateau 67B, and a second slope 67C. First slope 67A slopes away from the stack towards interior surface 61 to form a ramp. This allows second article 12 to slide along slope 67A and into plateau 67B in response to the lifting force. Desirably, the entire stack of articles is supported between lift portion 30 and plateau 67B, at least momentarily, as first article 10 is moved away. Second slope 67C further coordinates this movement. The shape of guide element 65 may vary. In FIG. 14B, for example, guide element 65 has a guide surface 165 is curved so that second article 12 can be slid along guide surface 165 in a similar manner.

Figure 13:
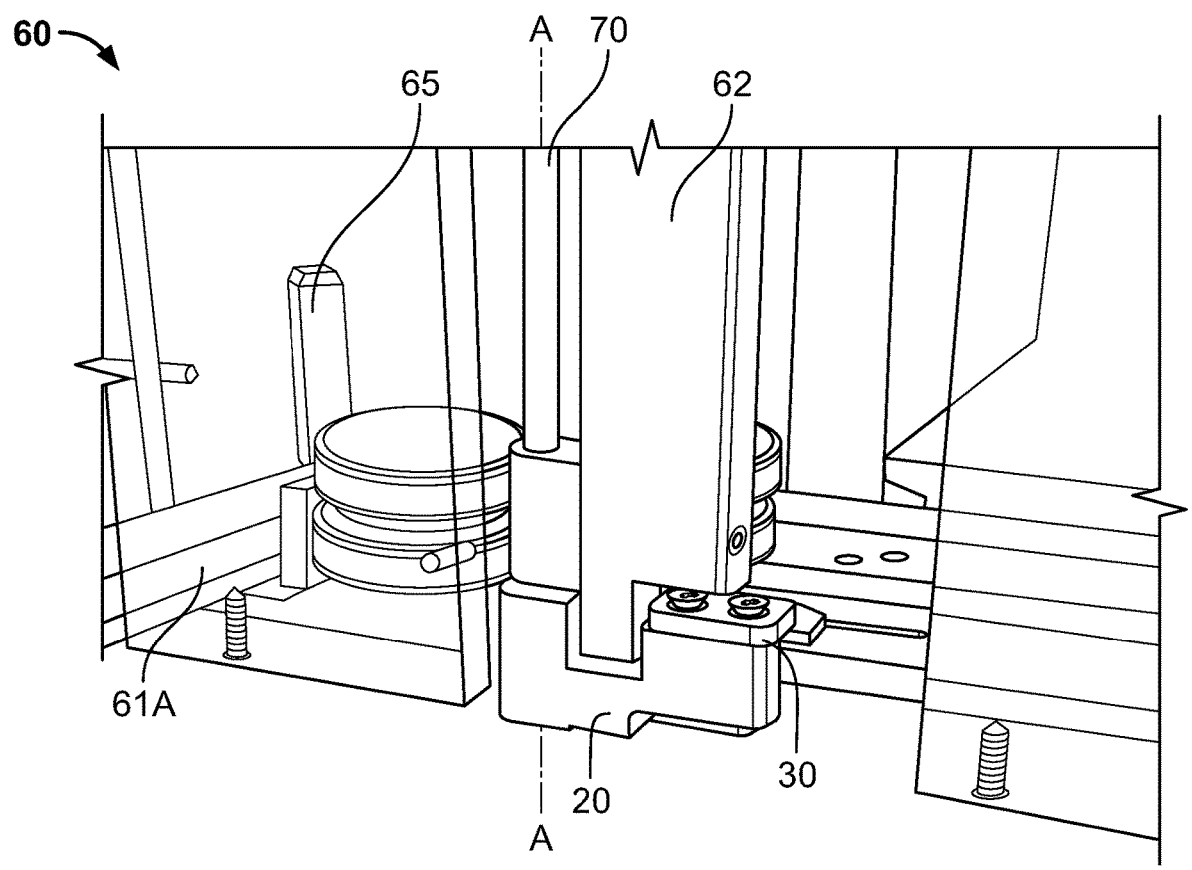
FIG. 13 provides a side view of the housing, the moveable door, and the lifter.

As noted above, both of lifter 20 and moveable door 62 may be rotated and lifted along a common axis. These movements are preferably coordinated. For example, door 62 of FIG. 1 is rotated into the support position just before lifter 20 is rotated into the contact position. This first movement ensures that the stack of articles will be stabilized before contact surface 15 is engaged by lifter 20. Alternatively, moveable door 62 and lifer 20 may be moved into their respective support and contact positions simultaneously and then raised together. In some embodiments, moveable door 62 is rotated into the support position and then raised with lifter 20 for a pre-determined amount of time to stabilize the lifted stack while first article 10 is extracted. After the pre-determined time, door 62 is then lowered with lifter 20 to stabilize the stack of articles while second article 12 assumes the position of first article 10 (FIG. 13).

Embodiments of the Lifting Mechanism

Lifting mechanism 80 provides an exemplary means for coordinating the movement of lifter 20 and moveable door 62 in and out of their respective contact and support positions. Although described below with reference to actuators and the like, it should be appreciated that a person skilled in the art would recognize that lifting mechanism 80 may incorporate any combination of components adapted to move lifter 20 and door 62 in order to perform the functions described herein. It should be further appreciated that aspects of the support systems for each element of lifting mechanism 80 described herein are largely a matter of design choice. Therefore, a person of ordinary skill in the art would understand that specific support configurations and dimensions are not critical to the operation and movements of lifter 20 and door 62 described in this application. Moreover, it is contemplated that the elements of system 1, including any embodiment of lifting mechanism 80, may be part of an automated assembly line; wherein a plurality of articles are rapidly stacked and then individually removed and conveyed elsewhere for processing. Thus, the specific support configurations described herein may also be modified to accommodate aspects of the automated assembly line.

One embodiment of lifting mechanism 80 is adapted to move lifter 20 and moveable door 62 in a continuous cycle of movement. As shown in FIG. 2, for example, lifting mechanism 80 has an elongated rod 70 that is operatively attached to lifter 20 and moveable door 62. Rod 70 desirably allows for movement of lifter 20 and moveable door 62 about axis A-A of FIG. 2. As described fully below, each of lifter 20 and door 62 are preferably adapted to move independently of one another.

Figure 6:
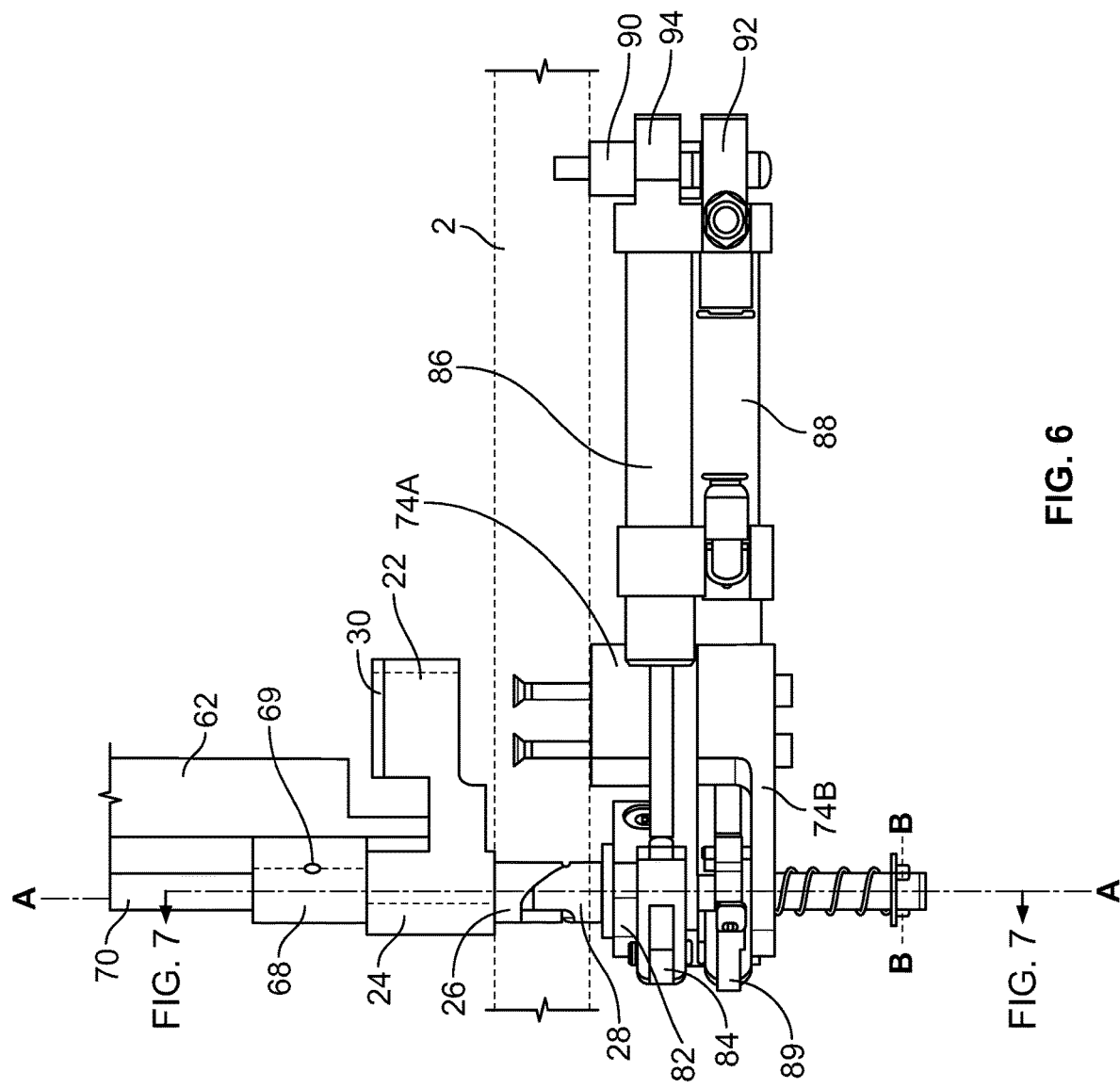
FIG. 6 is a side view of the elements shown in FIG. 5.

In FIGS. 2-5, for example, rod 70 is supported between a top bracket 72 and a bottom bracket 74. Preferably, bottom bracket 74 comprises a first bottom bracket 74A disposed opposite of a second bottom bracket 74B along axis A-A. Dividing bracket 74 into modular pieces 74A and 74B allows its dimensions to be easily modified and simplifies any subsequent repair efforts. Each of the top and bottom brackets 72 and 74 are rigidly attached to support elements external to system 1, such as exemplary ceiling surface 3 (FIG. 3) or table surface 2 (FIG. 6). In FIGS. 3 and 6, for example, at least one fixing element is used to attach each of top bracket 72 to ceiling surface 3 and bottom bracket 74 to table surface 2.

Figure 4A:
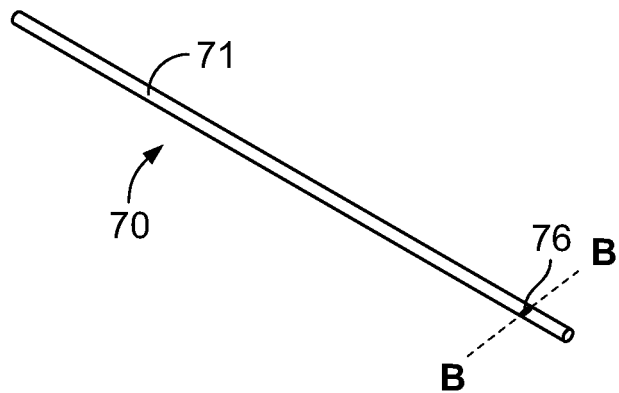
FIGS. 4A-B provide perspective and plan views of an elongated rod element of the lifting mechanism.
Figure 4B:
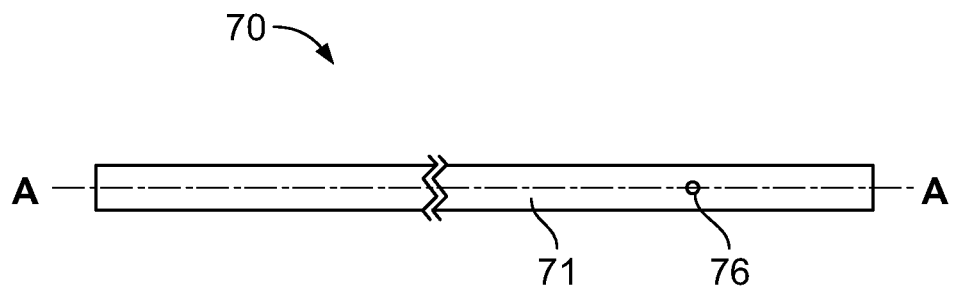

Rod 70 is rotatably and slidably engaged to the top and bottom brackets 72 and 74. This allows rod 70 to be rotated about and moved along longitudinal axis A-A while supported by brackets 72 and 74. Preferably, as shown in FIG. 4A, rod 70 has a circular cross-section with an exterior surface 71 with frictional characteristics similar to that of a polished metal. This allows elements of system 1 to be slidably or rotatably engaged with rod 70 in the manner set forth below.

Movable door 62 is depicted in FIGS. 2 and 4-5, for example, as being fixed to and rotatable with rod 70. As illustrated, moveable door 62 is rigidly attached to rod 70 by top bracket 64 and bottom bracket 68. Each bracket 64, 68 preferably has an interior surface that defines a bore 64A or 68A that is sized to receive rod 70 along axis A-A. Brackets 64 and 68 also have set screw hole 66 or 69 that is sized to receive a set screw along an axis parallel to exemplary axis B-B. The set screw is adapted to affix brackets 64 and 68 to rod 70. As best shown in FIG. 5, moveable door 62 desirably has an end portion 63 that fits into a groove 23 of lifter arm 22 to provide a continuous stabilizing surface.

Figure 7:
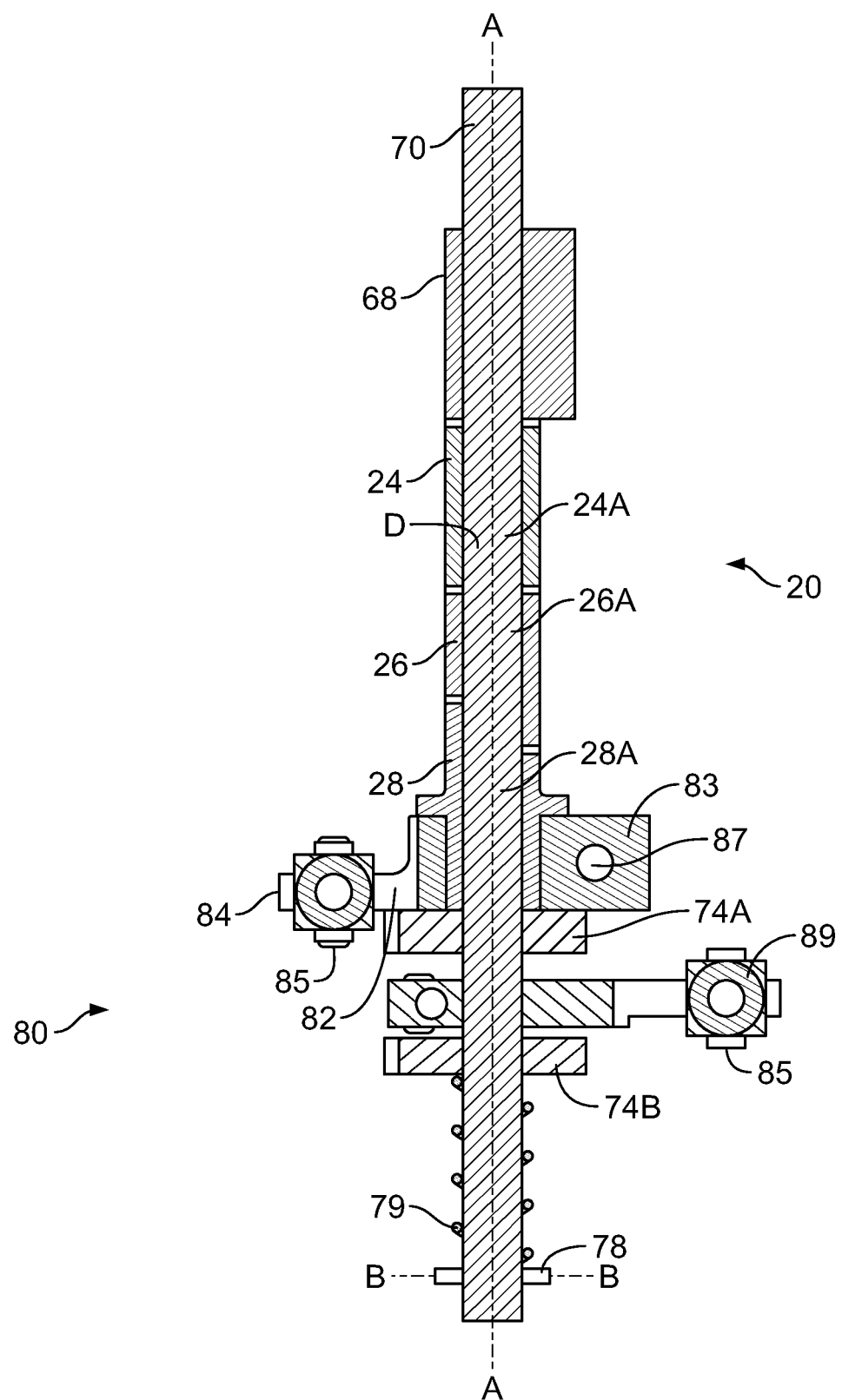
FIG. 7 is a section view of the elements shown in FIG. 7 along the section line 7-7 of FIG. 6.

An exemplary connection between lifter 20, lifting mechanism 80, and moveable door 62 is illustrated in FIGS. 5-7 and 10-11. For example, in FIG. 5, lifter arm 22 of lifter 20 has an end portion 24 with an interior surface that defines a bore 24A. Bottom bracket 68 is placed adjacent end portion 24 of lifter arm 22 so that any lifting forces applied by an element of lift mechanism 80 to raise end portion 24 may also be utilized to raise bottom bracket 68 and, thus, moveable door 62 and rod 70. End portion 24 is assembled with an upper bushing 26 having an interior surface that defines a bore 26A. A lower bushing 28 is disposed opposite of upper bushing 26. Bushing 28 also has an interior surface that defines a bore 28A. As shown in FIG. 7, each of bores 24A, 26A, and 28A have the same diameter and are coaxial with axis A-A. Bores 24A, 26A, and 28A rotate independently of rod 70, whereas bottom bracket 68 of moveable door 62 is rigidly attached to rod 70 and rotatable therewith. Thus, rotating rod 70 positions movable door 62 in the support position independent of end portion 24, upper bushing 26, and lower bushing 28.

Figure 10:
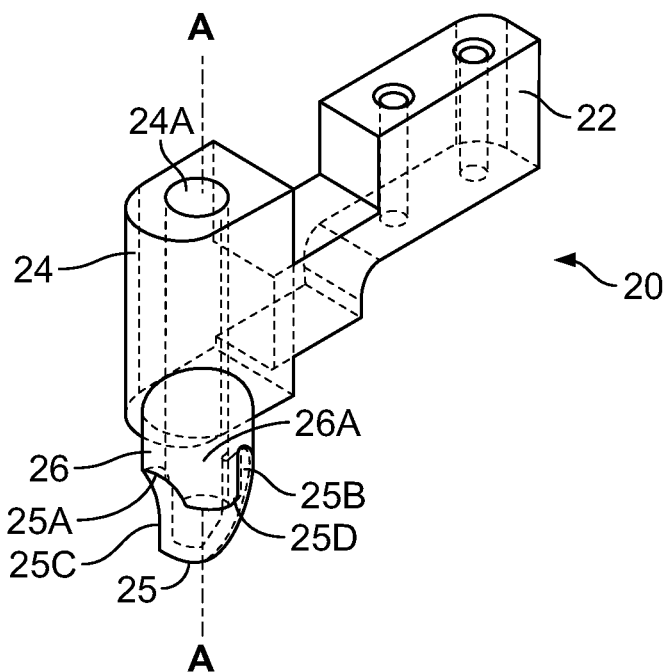
FIG. 10 provides a phantom view of an lifter arm element of the lifter.
Figure 11:
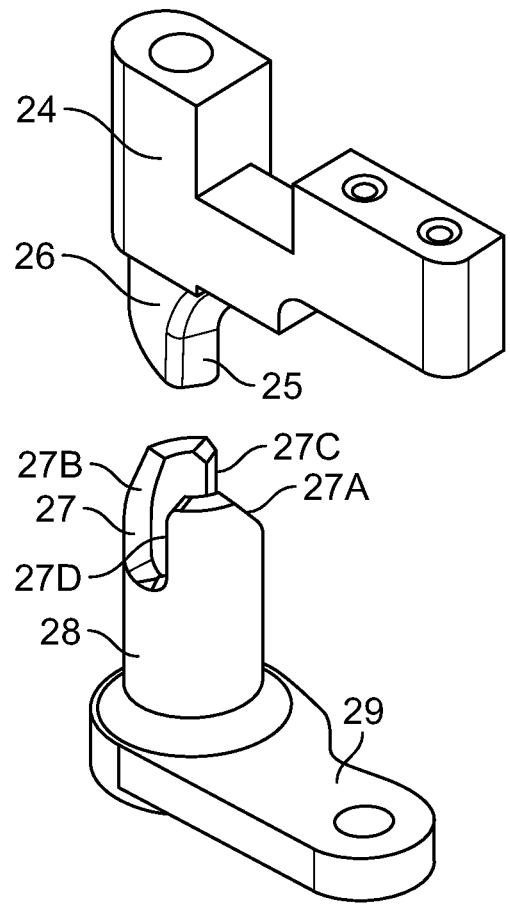
FIG. 11 provides an exploded view of the lifter arm of FIG. 10 assembled with an element of the lifting mechanism.

Bushings 26 and 28 are adapted to move lifter 20 into the contact and lifted positions, preferably in a continuous motion. As shown in FIGS. 10-11, upper bushing 26 has an irregular lower surface 25. Preferably, surface 25 is engageable with an irregular upper surface 27 of lower bushing 28 so that the interaction of surfaces 27 and 28 drives the continuous cycle of motion. For example, in the embodiment of FIGS. 10-11, lower surface 25 is rotated to interact with upper surface 27. This interaction rotates upper bushing 26 and attached lifter arm 22. Each surface 25 and 27 is adapted to promote this interaction. For example, as shown in FIG. 10, surface 25 of upper bushing 26 is an irregular, undulating driving surface with a first slope 25A opposite of a second slope 25B. Each slope 25A and 25B is opposite of a respective first edge 25C and second edge 25D. Irregular upper surface 27 of lower bushing 28 is also illustrated as having a set of first and second slopes 27A and 27B opposite of a set of ledges 27C and 27D, as shown in FIG. 11. Therefore, when lower bushing 28 is rotated about axis A-A, each of ledges 27C and 27D of irregular upper surface 27 will apply a rotational force to ledges 25C and 25D that rotates upper bushing 26 and, thus, lifter arm 22.

When lifter arm 22 is in the contact position, further rotation of lower bushing 28 raises the lifting arm 22 and moveable door 62 above the contact position. For example, moving lifter arm 22 into the contact position causes second article 12, which is captured between lifter arm 22 and interior surface 61, to apply reaction force that acts against the driving forces applied by ledges 27C and 27D to ledges 25C and 25D. While the frictional forces between driving surfaces 25 and 27 are sufficient to rotate lower bushing 28, these same forces are overcome under the influence of this reaction force. Therefore, further rotation of lower bushing 28 will cause slopes 25A and 25B to slide over ledges 27C and 27D to ride along the upward path defined by slopes 27A and 27B. Because lifter arm 22 cannot be further rotated when in the contact position, upper bushing 26 is compelled upward along axis A-A upon further rotation of lower bushing 28. As described above with reference to FIG. 7, upper bushing 26 is assembled to end portion 24, upon which bottom bracket 68 of moveable door 62 rests. Thus, in this embodiment, moveable door 62 and rod 70 are also lifted by further rotation of lower bushing 28 after lifter arm 22 is in the contact position.

An exemplary means for rotating lower bushing 28 is depicted in FIGS. 2 and 5-8 as a first actuator 86 that is adapted to apply a linear force to a first actuator arm 82. Preferably, first actuator is a hydraulic cylinder operable to apply and remove the linear force in a relatively smooth manner. This linear force is converted by lifting mechanism 80 into the rotational force described above. As shown in FIGS. 5 and 7, for example, lower bushing 28 is rigidly attached to first actuator arm 82, which has a lower surface adjacent the first bottom bracket 74A. Lower bushing 28 is preferably clamped to first actuator arm 82. Arm 82 has a clamping portion 83 depicted in FIGS. 5 and 7 as split to permit insertion of the bottom portion of lower bushing 28 therein. First actuator arm 82 has a bore 87 that extends through each half of clamping portion 83 to receive the exemplary bolt depicted in FIG. 5. This allows lower bushing 28 to be fixed to first actuator arm 82 by tightening the exemplary bolt. Tightening clamping portion 83 does not limit the ability of lower bushing 28 to rotate about or slide along the exterior surface of rod 70. As illustrated, the end portion 84 of first actuator 86 is rotatably connected to an open end of first actuator arm 82 by a pin 85. This allows lower bushing 28 to rotate in response to the linear motion of actuator 86.

Figure 8:
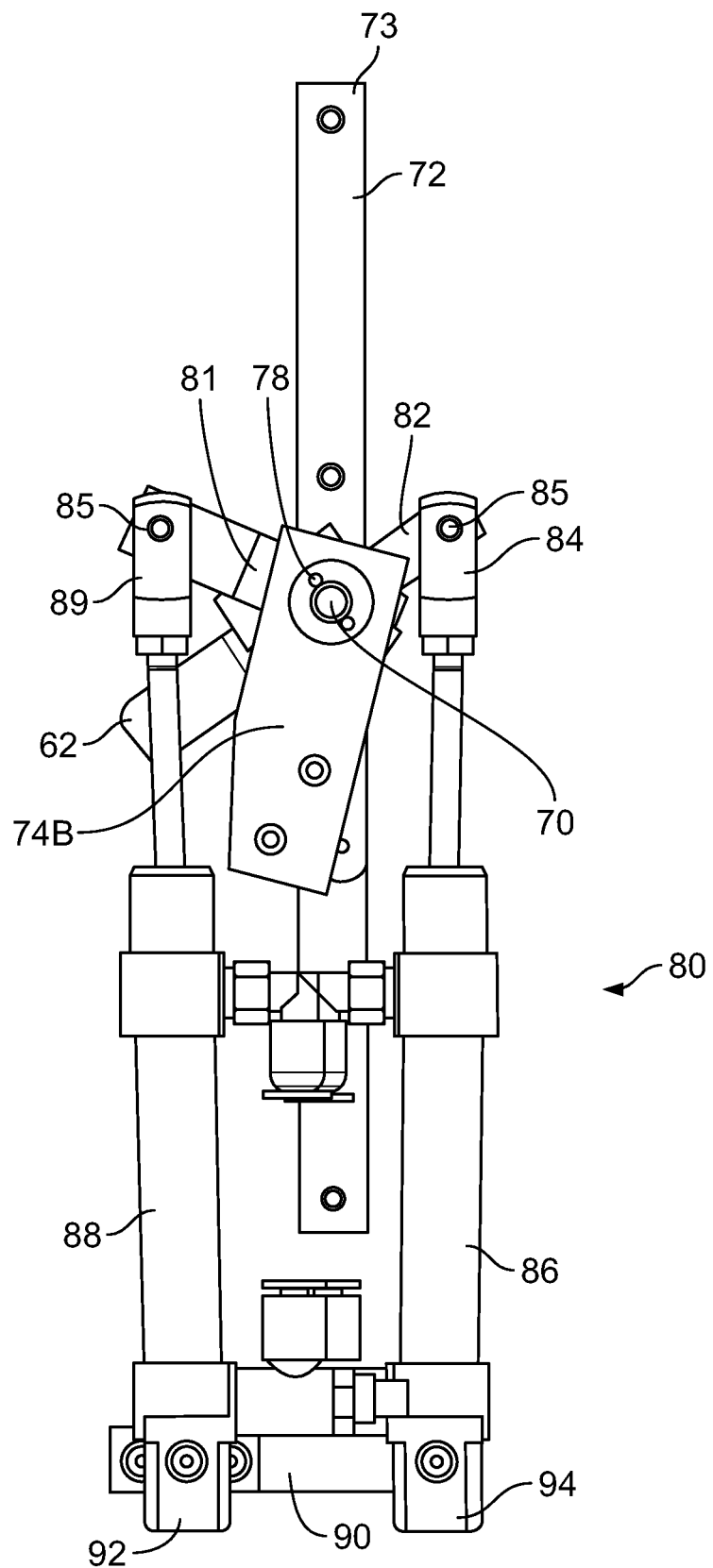
FIG. 8 is a bottom-up view of the lifting mechanism.

A similar means for rotating moveable door 62 is also contemplated. For example, as shown in FIG. 8, a second actuator 88 is adapted to rotate rod 70 and, thus, moveable door 62. It should be noted that actuator 86 is on the left in FIG. 5, yet on the right in the bottom-up view provided by FIG. 8. As illustrated, second actuator 88 is depicted as having an end portion 89 that is rotatably connected to an open end of a second actuator arm 81 by another pin 85. The opposite end of second actuator arm 81 is rigidly attached to rod 70. For example, actuator arm 81 may be clamped to rod 70 using a set screw, much like brackets 64 and 66 of moveable door 62. Similar to the above, this connection utilizes the linear forces applied by second actuator 88 to second actuator bracket 81 to rotate rod 70 together with moveable door 62.

Figure 12B:
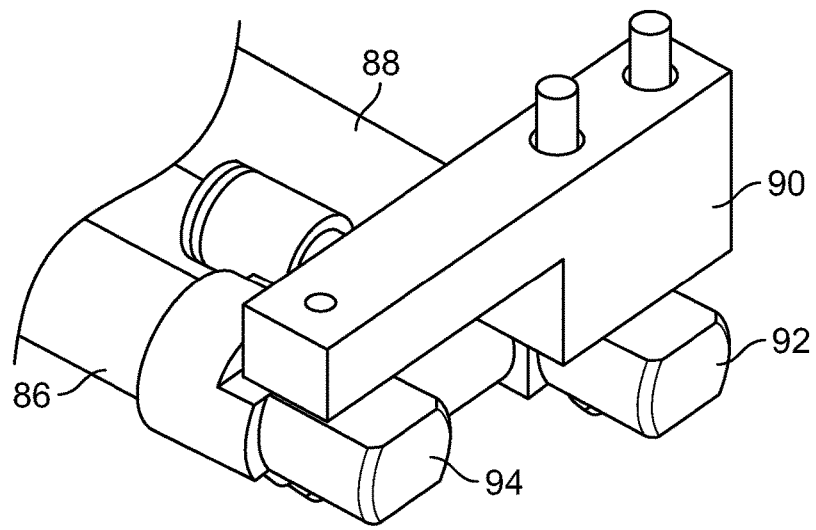
FIG. 12B provides a side view of a bracket element for the lifting mechanism described herein.

To apply the linear forces described above, both of the first and second actuators 86, 88 are attached to exemplary table surface 2. This surface 2 may be assumed to be any rigid element adapted to support the weight of system 1 and counter all of the linear forces applied by actuators 86 and 88. As shown in FIGS. 2, 6, and 12B, a reaction end 94 of first actuator 86 and a reaction end 92 of second actuator 88 are attached to surface 2 by an actuator support bracket 90. As illustrated, bracket 90 is rigidly attached to table surface 2 by inserting a of fixing element into each bore extending through bracket 90 and surface 2 and then tightening the fixing elements. This ensures that each of reaction ends 92 and 94 may be attached to bracket 90 so that the respective first and second actuators 86 and 88 are fixed against linear translation with respect to table surface 2.

At least one of the first or second actuators 86 or 88 may tilt relative to surface 2 as rod 70 is lifted in the manner described above. Therefore, in some embodiments, each reaction end 92 and 94 is rotatably attached to bracket 90. For example, in FIG. 12B, each of reaction end 92 and 94 are suspended from bracket 90 so as to prevent linear translation relative to surface 2, as noted above. To permit rotation, either reaction end 92 or 94 may have a resilient bushing material that surrounds the fixing element within the bore. Desirably, portions of this bushing may be compressed within the bore to allow either reaction end 92 or 94 to rotate independently of bracket 90, as needed, to accommodate the lifting motions described herein. Of course, any known manner of establishing a rotatable connection between bracket 90 and reaction ends 92 or 94 may be similarly employed without departing from the present invention.

An end portion 77 of rod 70 dampens the movement of rod 70 along axis A-A. For example, rod 70 in FIGS. 4A-B has an interior surface that defines a bore 76 extending along an axis B-B that is transverse with longitudinal axis A-A. A spring element 79 is captured between second bottom bracket 74B and a support ring 75. In FIG. 5, for example, pin 78 is inserted into bore 76 along axis B-B to prevent the support ring 75 from sliding upward or downward along axis A-A with respect to rod 70 when subjected to the expansive forces of spring element 79. Because second bottom bracket 74B is rigidly attached to surface 2, spring element 79 dampens the movements of rod 70 along axis A-A so as to further ensure lifter arm 22 is moved in a continuous, fluid manner. For example, spring element 79 may be compressed as rod 70 is lifted so as to apply a dampening counter force that absorbs any irregular motions introduced by the interaction of irregular surfaces 25 and 27.

Alternative Embodiments and Related Inventions

Alternate embodiments of various elements of the system 1 are also described below as part of a system 100. Related methods and kits are also described with reference to the various elements of lifter 20, extractor 40, and housing 60 described above. Wherever possible, like reference numbers have been used to describe similar elements of system 1, except within the corresponding 100 series of numbers. Of course, any features described with reference to these alternative embodiments or related inventions might be incorporated into any embodiment of any system described in this application.

Figure 9A:
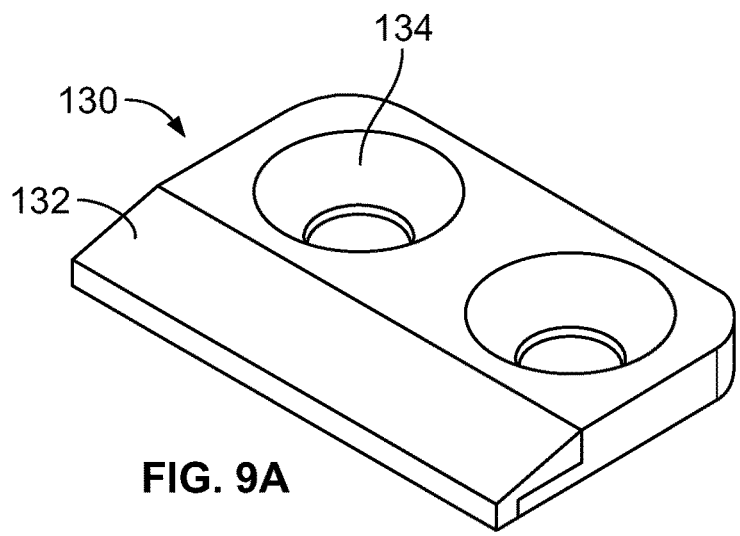
FIGS. 9A-C provide perspective, plan, and side views of a removable tip attached to the lifter.
Figure 9B:
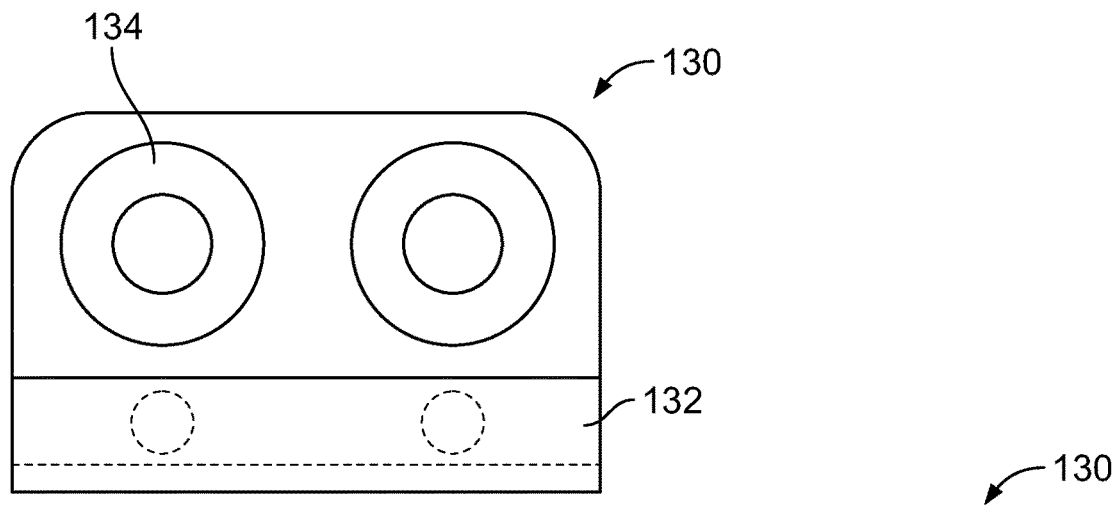
Figure 9C:
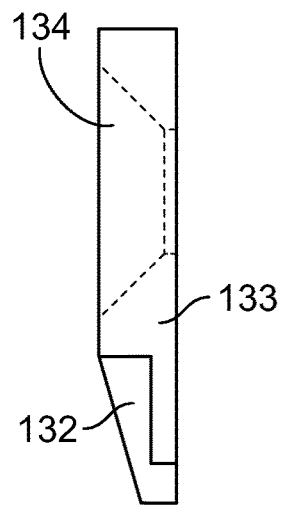

As noted above with reference to FIGS. 9A-C, lift surface 30 of lifter 20 may be a removable tip 130. It should be understood that tip 130 may be removably attached to arm 22 in any one of a variety of ways. In one embodiment, as shown in FIGS. 9A-C, tip 130 has at least one receiving bore 134 extending therethrough. Preferably, lifting arm 22 has at least one threaded bore that is coaxially aligned with bore 134. This allows removable tip 130 to be attached to lifter arm 22 by inserting a fixing element into bores 134 Like surface 30, the entirety of removable tip 130 may be made from a composition selected from a group consisting of silicone, urethane, a like material, and a combination thereof. Alternatively, only a portion of surface or tip 130, such as contact portion 132, may be composed of such a composition.

In FIGS. 9A-C, removable tip 130 is shaped to insert between the first and second articles 10 and 12. For example, tip 130 is depicted as having a triangularly shaped cross-section 133 that wedges between bottom surface 13 of second article 12 and top surface 11 of first article 10 when the lifter 20 is in the contact position. This allows tip 130 to apply at least a portion of the lifting force to bottom surface 13 of second article 12. If, for example, first and second articles 10 and 12 are nested together by a nesting feature, then cross-section 133 may also be adapted to disrupt the nesting feature by wedging between articles 10 and 12. In this instance, the coefficient of friction between tip 130 and the bottom surface 13 of second article 12 ensures that article 12 will remain engaged with tip 130 as it is lifted along axis A-A, at least until first article 10 is moved away from the stack of articles.

Figure 16:
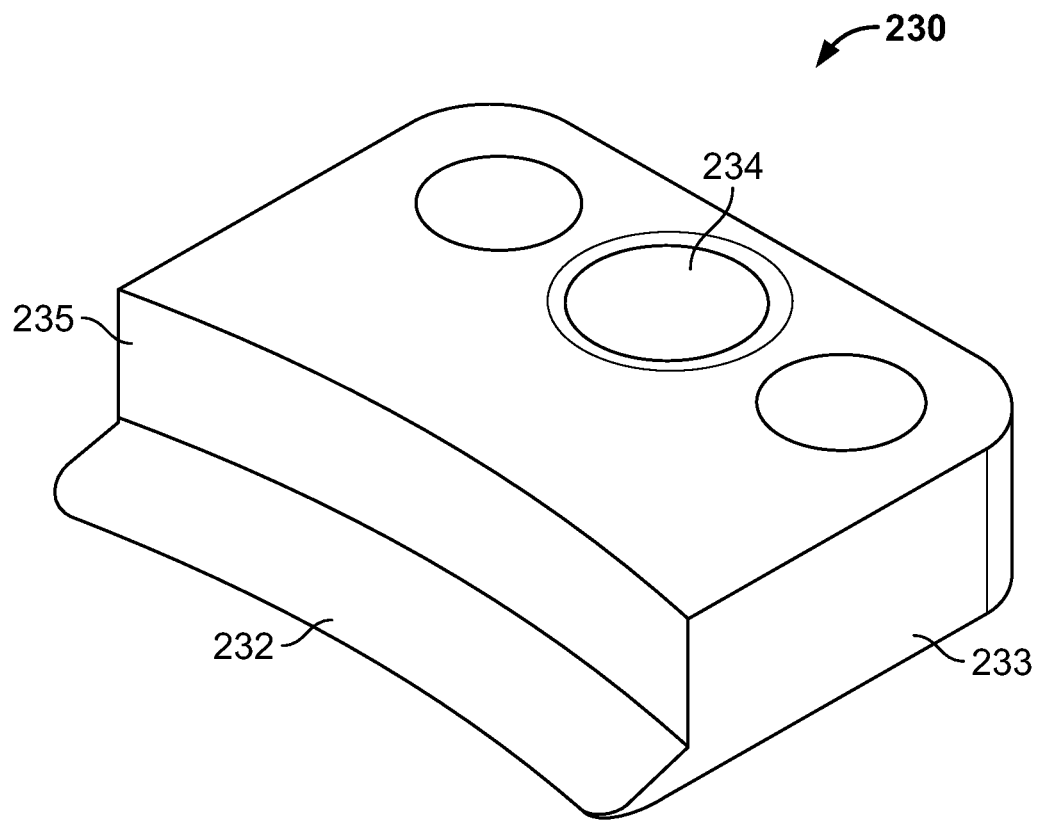
FIG. 16 depicts an alternate embodiment of an element of the lifter.

Alternative embodiments of removable tip 130 are also described in this application. For example, a tip 230 is illustrated in FIG. 16 as having an irregularly shaped cross-section 233 with a first contact portion 232 and a second contact portion 235. As shown, both of the first and second contact portions 232 and 235 are curved to substantially conform to the outer diameter of articles 11 and 12. This configuration allows tip 230 of FIG. 16 to both raise second article 12 and further stabilize article 12 as it is raised. For example, first portion 232 extends outwardly from tip 230 so that it may be wedged between articles 11 and 12 when lifter 20 is moved into the contact position. Second portion 235 will be adjacent contact surface 15 of second article 12 once first portion 232 has been wedged in this manner. Thus, first portion 232 may be used to lift the stack, while second portion 235 may be used to stabilize the stack. The height of second portion 235 is depicted in FIG. 16 as being relative to the height of article 12. In still other alternative embodiments, second portion 235 may be sized relative to a portion of the entire stack and, thus, much taller.

Variations of extractor 40 are also contemplated. Although depicted has having a pair of retractable arms 42, extractor 40 may be any device that is moveable relative to table surface 2 and adapted to move first article 10 away from the stack. For example, the extractor 40 might alternatively be a conveyer mounted on table 2. Elements of retractable arm 42 may also be modified. For example, arm 42 may alternatively be an elongated arm with a hook that is adapted to pull first article 10 along axis D-D without folding back onto itself.

Numerous variations of housing 60 are also possible. For example, the planar elements of interior surface 61 might have a curvilinear shape. Alternatively, housing 60 may be comprised of plurality of elongated rods, each rod having an exterior surface that coincides with stack perimeter 16. Similar to above, this alternative configuration provides a three point retention system, wherein each of the first and second rods, as well as moveable door 62, are positioned about perimeter 16 in a triangular fashion to guide and stabilize the stack of articles as it is lifted.

Figure 15:
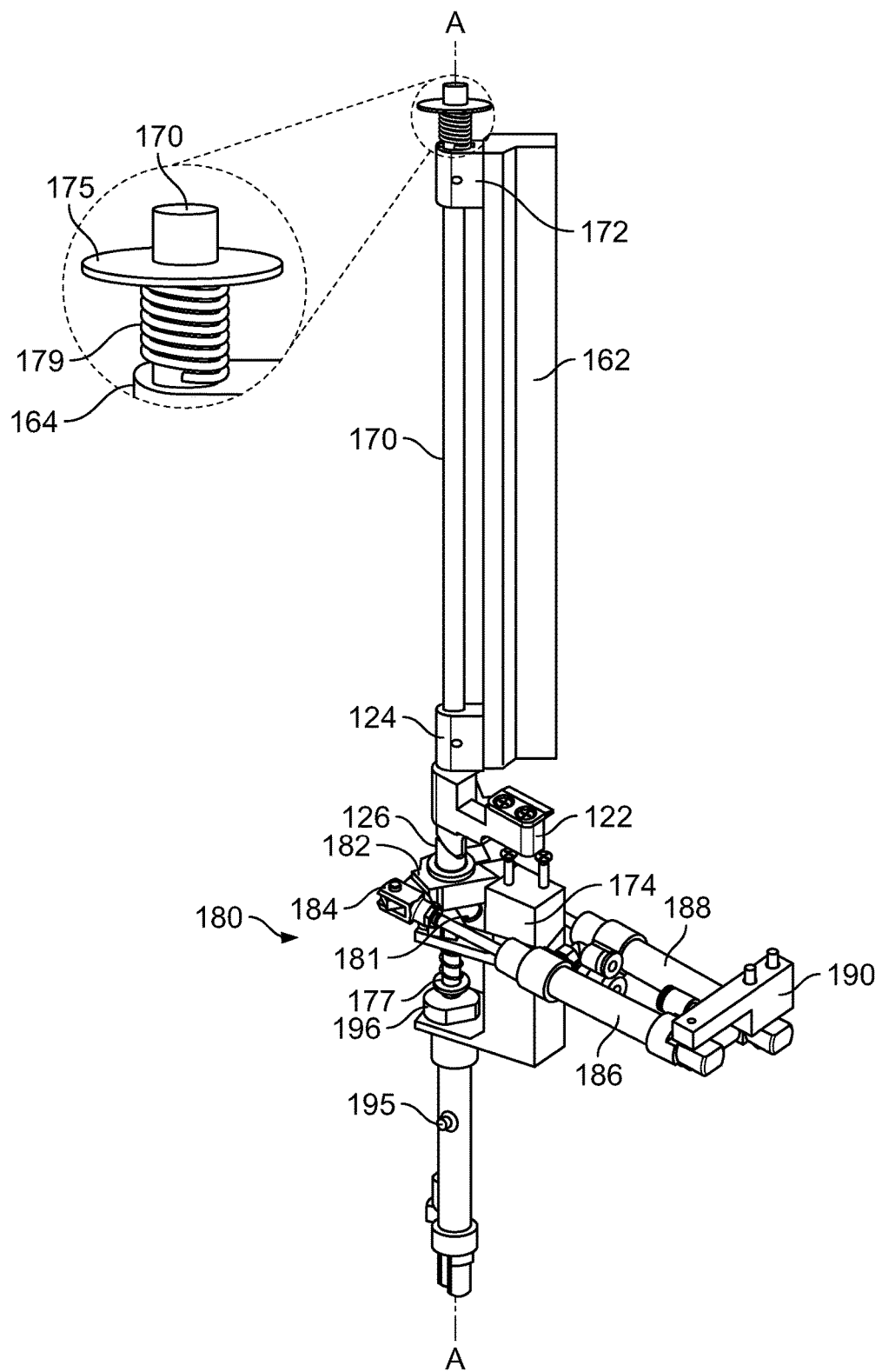
FIG. 15 is a detailed view of an alternate lifting mechanism.

An alternative lifting mechanism 180 is depicted in FIG. 15. In this exemplary embodiment, lifting mechanism 180 has an elongated rod 170 attached to a third actuator 195, which is preferably a hydraulic cylinder adapted to apply a lifting force to rod 170 along axis A-A. Similar to above, rod 170 is supported between a top bracket 172 and a bottom bracket 174. In this embodiment, however, the top of rod 170 is adapted to dampen the movements of rod 70 in any direction along axis A-A. Preferably, a spring element 179 is captured between a support rig 175 (top bracket 172) and a top bracket 164 attached to a moveable door 162. Thus, similar to above, spring element 179 may be used to ensure that rod 70 moves in a fluid manner. Although not shown in FIGS. 2-3, the top of rod 70 might alternatively be dampened by incorporation of a similar dampening feature into the workings of top bracket 72.

Lifter arm 122 of FIG. 15 has an end portion 124 adjacent to a moveable door 162. End portion 124 is rigidly connected to a single bushing 126 in FIG. 15 because lift cylinder 195, and not driving surfaces 25 and 27, is adapted to move rod 170 along axis A-A. Similar to the above, each of end portion 124 and single bushing 126 preferably has a bore with a common diameter that is coaxial with axis A-A and sized to slidably and rotatably receive rod 170 therein.

As also shown in FIG. 15, a first actuator 186 has an end portion 184 that is rotatably attached to a first actuator arm 182. First actuator arm 182 is preferably clamped to single bushing 126 so that the linear forces applied by first actuator 186 may be used to rotate lifter arm 122 about axis A-A. Preferably still, bushing 126 is rotatable and slidable along rod 170 when clamped to first actuator arm 182. As shown in FIG. 15, a second actuator 188 is rotatably attached to a second actuator arm 181. Like arm 81 described above, a portion of the second actuator arm 181 is also rigidly attached to rod 170. This ensures that the linear forces applied by second actuator 188 may be used to rotate rod 170 and, thus, moveable door 162, which is also attached to rod 170. Likewise, the reaction ends of actuators 186 and 188 are preferably attached to a surface, like table 2, via a support bracket 190 adapted to fix the actuators against linear translation.

In this embodiment, bottom bracket 174 is further adapted to support third actuator 195. For example, in FIG. 15, the bottom portion of bracket 174 has a fork with extensions separated to capture third actuator 195 therebetween. This allows actuator 195 to slide between the extensions and for assembly with bracket 174. For example, the top portion of actuator 195 may have a rim opposite of a threaded portion along axis A-A. In this configuration, a nut may then be threaded onto the threaded portion of actuator 195 and tightened against the extensions of bracket 174 to secure actuator 195 thereto.

Third actuator 195 is preferably attached to end portion 177 of rod 170. Such attachment will ensure stable interaction between actuator 195 and rod 170 using any conventional means known to those skilled in the art. In this embodiment, first actuator 186 is used to rotate lifter arm 122, while second actuator 188 is used to rotate moveable door 162, and third actuator 195 is used to lift arm 122 and door 162. Accordingly, lifting mechanism 180, like mechanism 80, allows lifter arm 122 to be rotated in a single, continuous movement comparable to that provided by bushings 26 and 28.

A person of ordinary skill in the art would also recognize that, as a matter of design choice, numerous types of actuators may be used to move the novel aspects of lifter 20 or 120 and housing 60 or 160 described herein. For example, the rotational movements enabled by actuators 86 and 88 might alternatively be applied by a set of electric motors that are operably coupled to lifting arm 22 and moveable door 62. As a further example, third actuator 195 might also be rotatably attached to lower bracket 174 and an electric motor adapted to rotate rod 170 and actuator 195 about axis A-A, thereby eliminating the need for second actuator 188.

Any combination of the elements described above with reference to FIGS. 1-13 may also be packaged within a retrofit kit adapted to add the capabilities of lifter 20 and lifting mechanism 80 to an existing system. Such a kit may include any elements of lifter 20 or mechanism 80 described above. For example, to retrofit an existing system to have the capabilities of system 1, such a kit may include a lifter arm 22, upper bushing 26, lower bushing 28, first actuator 86, first actuator arm 82, support bracket 90, spring 75, and a plurality of fixing elements. If tip 30 is replaceable, then such a kit may also include a plurality of replaceable tips 30. As a further example, to retrofit an existing system to have the capability of system 100, such a kit may alternatively include a lifter arm 122, single bushing 126, first actuator 186, first actuator arm 182, support bracket 190, spring 175, third actuator 195, and a plurality of fixing elements. Likewise, a plurality of tips 130 may also be included. Of course, any combination of the elements set forth herein with respect to system 1 or 100 may also be included depending upon the capabilities of the existing system. Preferably, each element of a kit in accordance with this invention is further packaged in suitable shipping container.

Although the inventions herein have been described with reference to particular embodiments, it is to be understood that these embodiments are merely illustrative of the principles and applications of the present inventions. It is therefore to be understood that numerous modifications may be made to the illustrative embodiments and that other arrangements may be devised without departing from the spirit and scope of the present inventions as defined by the appended claims.

The invention claimed is:

1. A separating system comprising:
a housing sized to receive a stack of articles having at least one second article stacked on top of a first article, wherein the housing has an interior surface and is shaped to at least partially surround the stack of articles above the first article,
a lifter rotatable into a contact position adjacent a surface on the at least one second article, the lifter being adapted to apply a lifting force to the surface on the at least one second article to lift at least a portion of the second article above the contact position; and
an extractor that moves the first article away from the stack of articles after the at least one second article has been lifted above the contact position by the lifter,
wherein the housing comprises a guide surface on the interior surface wherein the guide surface in cooperation with the lifter prevents the at least second one article from moving with the first article when the first article is moved by the extractor, and further wherein the housing guides the stack of articles downward after the first article is moved away and the lifter is rotated from the contact position and further wherein the housing is adjacent a moveable door that rotates from an open position to a closed position, wherein the moveable door, in the closed position, stabilizes the stack of articles as the first article is moved away by the extractor and wherein the moveable door is moved into the closed position before the lifter is moved into the contact position and wherein the moveable door is lifted in unison with the lifter after the lifter is moved into the contact position.

2. The separating system of claim 1, wherein the lifter has a tip engageable with a surface of the at least one first article.

3. The separating system of claim 2, wherein the tip is a removable tip.

4. The separating system of claim 3, wherein the removable tip is frictionally engageable with the surface of the at least one first article when the lifter is in the contact position.

5. The separating system of claim 4, wherein the removable tip is formed of urethane or silicone.

6. The separating system of claim 1, wherein the lifter is rotated into the contact position, and wherein the moveable door is rotated into the closed position independently from but in concert with the lifter to cooperate in stack stabilization.

7. A separating system comprising:
a housing sized to receive a stack of articles having at least one second article stacked on top of a first article wherein the housing is shaped to at least partially surround the stack of articles above the first article,
a lifter movable into a contact position adjacent a surface on the at least one second article, the lifter being adapted to apply a lifting force to the surface on the at least one second article to lift at least a portion of the second article above the contact position;
an extractor that moves the first article away from the stack of articles after the at least one second article has been lifted above the contact position by the lifter; and
a lifting mechanism with an elongated rod that is rotatably and slidably attached to the lifter and rigidly attached to a moveable door;
wherein the housing is adjacent the moveable door that rotates from an open position to a closed position, wherein the moveable door, in the closed position, stabilizes the stack of articles as the first article is moved away by the extractor and wherein the lifter is rotated into the contact position, and wherein the moveable door is rotated into the closed position independently from but in concert with the lifter to cooperate in stack stabilization.

8. The separating system of claim 7, wherein the lifter has an upper bushing engageable with a lower bushing that is rotatably attached to the elongated rod, and wherein rotation of the elongated rod moves the moveable door into the closed position and rotation of the lower bushing moves the lifter into the contact position.

9. The separating system of claim 8, wherein upper bushing has a lower driving surface engageable with an upper driving surface of the lower bushing so that further rotation of the lower bushing lifts the lifter and moveable door above the contact position in a continuous motion.

10. The separating system of claim 8, further comprising at least one first actuator adapted to rotate the lower bushing.

11. The separating system of claim 10, further comprising a second actuator operably attached to the elongated rod to rotate the moveable door.

12. A separating system comprising:
a housing sized to receive a stack of articles having at least one second article stacked on top of a first article, wherein the housing has an interior surface,
a lifter rotatable into a contact position adjacent a surface on the at least one second article, the lifter being adapted to apply a lifting force to the surface on the at least one second article to lift at least a portion of the second article above the contact position, wherein the lifter has a tip engageable with a surface of the at least one first article and wherein the tip is a removeable tip formed of urethane or silicone and is frictionally engageable with the surface of the at least one first article when the lifter is in the contact position and wherein the removable tip has a triangularly shaped cross-section adapted to wedge between a bottom surface of the at least one second article and a top surface of the first article when the lifter is in the contact position so as to apply at least a portion of the lifting force to a bottom surface of the second article; and
an extractor that moves the first article away from the stack of articles after the at least one second article has been lifted above the contact position by the lifter,
wherein the housing comprises a guide surface on the interior surface wherein the guide surface in cooperation with the lifter prevents the at least second one article from moving with the first article when the first article is moved by the extractor and wherein the housing guides the stack of articles downward after the first article is moved away and the lifter is rotated from the contact position.

13. The separating system of claim 12, wherein the extractor moves the first article away from the stack of articles while each at least one second article is at least partially supported by a guide element mounted to the housing.

14. The separating system of claim 13, wherein the extractor has at least one retractable arm that moves under and past the first article in a first direction while in a retracted position, said retractable arm being biased to open into an extraction position adjacent a side of the first article as the extractor moves in a second direction opposite to the first direction.

15. A separating system comprising:
a housing sized to receive a stack of articles having at least one second article stacked on top of a first article, wherein the housing has an interior surface, a lifter rotatable into a contact position adjacent a surface on the at least one second article, the lifter being adapted to apply a lifting force to the surface on the at least one second article to lift at least a portion of the second article above the contact position, wherein the lifter has a tip engageable with a surface of the at least one first article and wherein the tip is a removeable tip formed of urethane or silicone and is frictionally engageable with the surface of the at least one first article when the lifter is in the contact position; and an extractor that moves the first article away from the stack of articles after the at least one second article has been lifted above the contact position by the lifter wherein the extractor moves the first article away from the stack of articles while each at least one second article is at least partially supported by a guide element mounted to the housing and wherein the extractor has at least one retractable arm that moves under and past the first article in a first direction while in a retracted position, said retractable arm being biased to open into an extraction position adjacent a side of the first article as the extractor moves in a second direction opposite to the first direction wherein the housing comprises a guide surface on the interior surface wherein the guide surface in cooperation with the lifter prevents the at least second one article from moving with the first article when the first article is moved by the extractor and wherein the housing guides the stack of articles downward after the first article is moved away and the lifter is rotated from the contact position.

16. The separating system of claim 15, wherein the removable tip has a triangularly shaped cross-section adapted to wedge between a bottom surface of the at least one second article and a top surface of the first article when the lifter is in the contact position so as to apply at least a portion of the lifting force to a bottom surface of the second article.

17. The separating system of claim 15, wherein the stack of articles is formed in the housing by loading the first article under the at least one second article from a top of the housing.

18. The separating system of claim 17, wherein the stack of articles has a nesting feature that is at least partially nested when the stack is loaded into the housing, and wherein application of the lifting force disrupts the nesting feature.

* * * * *